United States Patent [19]

Galel

[11] Patent Number: 5,476,100

[45] Date of Patent: Dec. 19, 1995

[54] CATHETER STEERABLE BY DIRECTIONAL JETS WITH REMOTELY CONTROLLED CLOSURES

[75] Inventor: Zev Galel, Palo Alto, Calif.

[73] Assignee: Guided Medical Systems, Inc., Mountain View, Calif.

[21] Appl. No.: 271,879

[22] Filed: Jul. 7, 1994

[51] Int. Cl.⁶ .................................................. A61B 8/12
[52] U.S. Cl. ........................................ 128/662.06; 604/22
[58] Field of Search ................................. 604/21, 22, 30, 604/96, 99, 53, 102, 141, 167; 128/662.06, 660.03

[56] References Cited

U.S. PATENT DOCUMENTS

| | | | |
|---|---|---|---|
| 4,014,317 | 3/1977 | Bruno | 604/21 |
| 5,250,060 | 10/1993 | Carbo et al. | 604/22 |
| 5,256,141 | 10/1993 | Gencheff et al. | 604/21 |
| 5,333,614 | 8/1994 | Feiring | 128/662.06 |

*Primary Examiner*—George Manuel
*Attorney, Agent, or Firm*—Townsend and Townsend and Crew

[57] ABSTRACT

A catheter is provided with a directional steering capability by one or more jets ejecting fluid from the distal end of the catheter in a radial direction which causes the catheter tip to bend in the opposite direction by reaction force. Actuation of the jet is controlled by a closure valve at the jet orifice, the closure valve being driven by a signal transmitted from the proximal end of the catheter. Preferred signals are either fluid pressure signals or electrical signals.

27 Claims, 5 Drawing Sheets

CATHETER STEERABLE BY DIRECTIONAL JETS WITH REMOTELY CONTROLLED CLOSURES

This invention lies in the field of medical catheters and relates in particular to means for steering catheters to direct their distal tips into branched or convoluted bodily passages.

BACKGROUND OF THE INVENTION

Catheters are widely used in medical procedures, since they provide access to internal bodily passages and cavities for both diagnostic and therapeutic purposes without surgery. Catheters have proved valuable over the years for use in regions of the body such as the heart and coronary arteries, the brain, and the genito-urinary tract.

A critical procedure associated with the use of medical catheters is the insertion of the catheter into the body and the placement of the catheter tip at the appropriate location. Precise placement of the catheter tip is often critical to the success of the function the catheter is intended to perform, since the function must often be directed to a highly localized region of internal tissue while avoiding areas which are immediately adjacent. In addition, bodily passages are often of a very small diameter, and the interior wall of the passage is often delicate and susceptible to puncture. Steering capability is important, for example, in cardiovascular surgery when catheters are used as an alternative to bypass surgery to selectively remove plaque from arteries. The use of a catheter in these procedures offers significant benefits in terms of lower cost and lower risk. Steering capability is of particular importance in procedures involving peripheral arteries where plaque or thrombi are to be removed. In obstetrics and gynecology, catheters can be used in conjunction with dilatation and curettage procedures for the selective removal of excessive tissue and cyst growth, and directional control is important here as well. The same is true for the use of catheters for the delivery of site-specific treatments for ovarian cancer. Directional control is also important in urology procedures involving catheters. Examples of such procedures are the selective removal of prostate cancer and the treatment of urinary tract blockages infections. In certain oncology procedures, accurately guided catheters can be used for the selective removal of malignant tissue without affecting critical healthy tissue located nearby, and for improved biopsy methods, where it is important to reduce the incidence of trauma in healthy tissue. In neurosurgery, catheters can be used for the removal of intracranial hematomas and similar procedures, and precise directional control of the catheters is critical. In radiology, close directional control provides imaging and mapping catheters with active stabilization within the cardiac chamber. In internal body procedures in general, guided catheters are useful for such procedures as fluid aspiration to relieve abscesses and localized drug delivery. Other procedures and applications where steering capability is important will be readily apparent to the experienced medical practitioner.

Steering mechanisms have been devised for directing the distal tip of the catheter in a desired direction by remote control from the proximal end. One such mechanism includes a series of wires running the length of the catheter body on either side of its central axis and terminating in shims or thin strips at the distal end of the catheter. The operator steers the catheter by applying tension to one shim relative to the other, thereby causing the distal end to curve in the direction of the wire to which tension has been applied. The wires and the mechanism at the proximal end for selectively applying tension are unwieldy, however, and susceptible to breakage. Furthermore, they offer limited directional choice without twisting the entire catheter to achieve angular adjustments relative to the catheter axis.

Guidewires are widely used to assist in the placement of catheters in locations which are particularly difficult to reach. A guidewire is typically of very narrow diameter to fit within the lumen of a catheter. This permits the operator to slide the catheter over the guidewire after first directing the guidewire to the appropriate location. It also permits the operator to remove one catheter and replace it with another without removing the guidewire and hence without the cumbersome procedure of independently relocating the catheter tip to the region of interest. The steering of a guidewire is generally accomplished by constructing the guidewire to include a slight curvature at its distal tip, the tip being resilient in construction to resume the curvature when relaxed. This enables the operator to direct the guidewire tip laterally into branches of the vessel. To do this, however, the operator must rotate the guidewire from the proximal end so that the tip curves in the desired direction.

SUMMARY OF THE INVENTION

The present invention resides in a catheter with a steering capability which significantly reduces or eliminates the difficulties enumerated above, as well as other difficulties associated with catheter steering mechanisms of the prior art. Steering is accomplished by one or more jets of fluid at the catheter tip, directed radially outward and causing the catheter tip to move in an opposite direction due to the reaction force. Preferably, a plurality of jets are included, formed by a series of ports distributed around the circumference of the catheter. The bending of the catheter tip in any particular direction is achieved by selecting a jet to emerge from the opposing side of the catheter to the exclusion of the remaining jets. Further directional control can be achieved by using two or more adjacent jets so that the reaction force is opposite to the combined vector of the jets.

Fluid is supplied to all of the jets through a single lumen which extends the full distance to the catheter's distal end to communicate directly with each of the ports. The ports are individually and independently opened and closed by closures which are operated by signals transmitted from the proximal end of the catheter. The signals to operate the closures is transmitted to each closure independently of the remaining closures. The signals may be any of various types, the two most prominent being pressure signals and electrical signals. Closures actuated by pressure signals include pivoting closures and sliding closures, where pressure differentials govern the position of the pivot or of the sliding member. The same types of closures, and particularly sliding closures, may be actuated by electrical signals, by means analogous to electrically operated valves.

For embodiments in which the closures are operated by pressure signals, fluid pressure is transmitted to each closure independently of the remaining closures and of the fluid to the lumen supplying the jets themselves. In some of the preferred embodiments of the invention, the closures are operated by levers, and the fluid pressure which drives each closure imposes a pressure differential across the lever. The opening and closing of the closure is thus controlled by the imposition and direction of the pressure differential. The levers are part of the closure structure and are likewise located at the distal end of the catheter. Independent transmission of fluid pressure to each lever is achieved by individual lumens traveling the length of the catheter, each of these lumens being independent of the lumen supplying the jets. To distinguish among the various lumens, the term "primary lumen" is used in this specification to refer to the lumen supplying the jets, while the term "secondary lumens" is used to refer to the lumens supplying the fluid pressure which controls the closures.

The actuation of any single jet, and the selection among the various directional jets when a plurality of jets is present, is thus achieved by closures positioned at the sites of the jets themselves, i.e., at the distal end of the catheter, while the operation of these closures is achieved by remote control from the proximal end of the catheter. This offers a number of advantages to the operation and effectiveness of the directional control. For example, closures arranged and operating in this manner permit a quick response to signals from the proximal end of the catheter for changes of direction. Furthermore, the use of a single lumen supplying all of the jets rather than a series of lumens to supply each jet. individually permits one to use a jet supply lumen of a larger diameter without increasing the outer diameter of the catheter. With a larger diameter lumen, any frictional loss of jet fluid as the fluid flows the length of the catheter is substantially reduced. Still further, the control of the closures through secondary lumens which are separate from the primary lumen used for the jet supply permits the closures to be operated by pneumatic pressure, which can be transmitted more quickly and modulated with a faster response than liquid pressure as is preferably used in the jets themselves.

In embodiments of the invention that entail the use of pneumatic or other fluid pressure to actuate the closures, the supply of the fluid pressure to the individual closures on a selective basis is achieved by a series of valves which are operatively connected to the secondary lumens at the proximal end the catheter. The valves are individually controlled in any of a variety of ways known to those skilled in the art, and their selection may be conveniently governed by a manually or electronically operated directional selector.

The term "fluid" is used herein to include both gases and liquids. One or the other will be preferred in specific applications, depending on the region of the body into which the catheter is to be directed.

The term "catheter" is used herein to include both functional catheters and guidewires. The invention thus extends to guidewires whose sole purpose is to be directed to a particular situs in a bodily vessel and once at that situs to serve as a guide for insertion of a functional catheter to the same situs. The invention likewise extends to functional catheters themselves which may be used without a separate guidewire, the functional catheters containing any of a variety of functional elements for either diagnostic or therapeutic purposes. The catheters of this invention may thus contain additional lumens serving functions unrelated to the directional jets, or additional transmitting elements for transmitting signals such as optical or electronic signals from the distal end of the catheter to the proximal end, or both lumens and transmitting elements.

Additional features and advantages of the invention will be apparent from the description which follows.

DETAILED DESCRIPTION OF THE INVENTION AND PREFERRED EMBODIMENTS

While the invention is broad in scope and defined as indicated above by certain parameters each of which entails a range of variations, the invention is best understood by detailed descriptions of specific examples. Five such examples are shown in the drawings.

Figure 1:
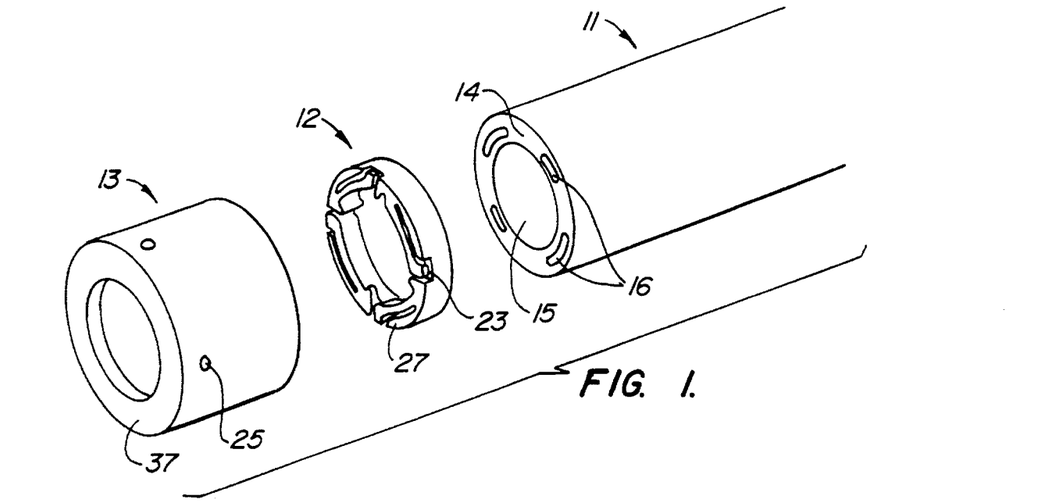
FIG. 1 is an exploded view in perspective of the distal end of one example of a catheter constructed in accordance with the present invention.
Figure 2:
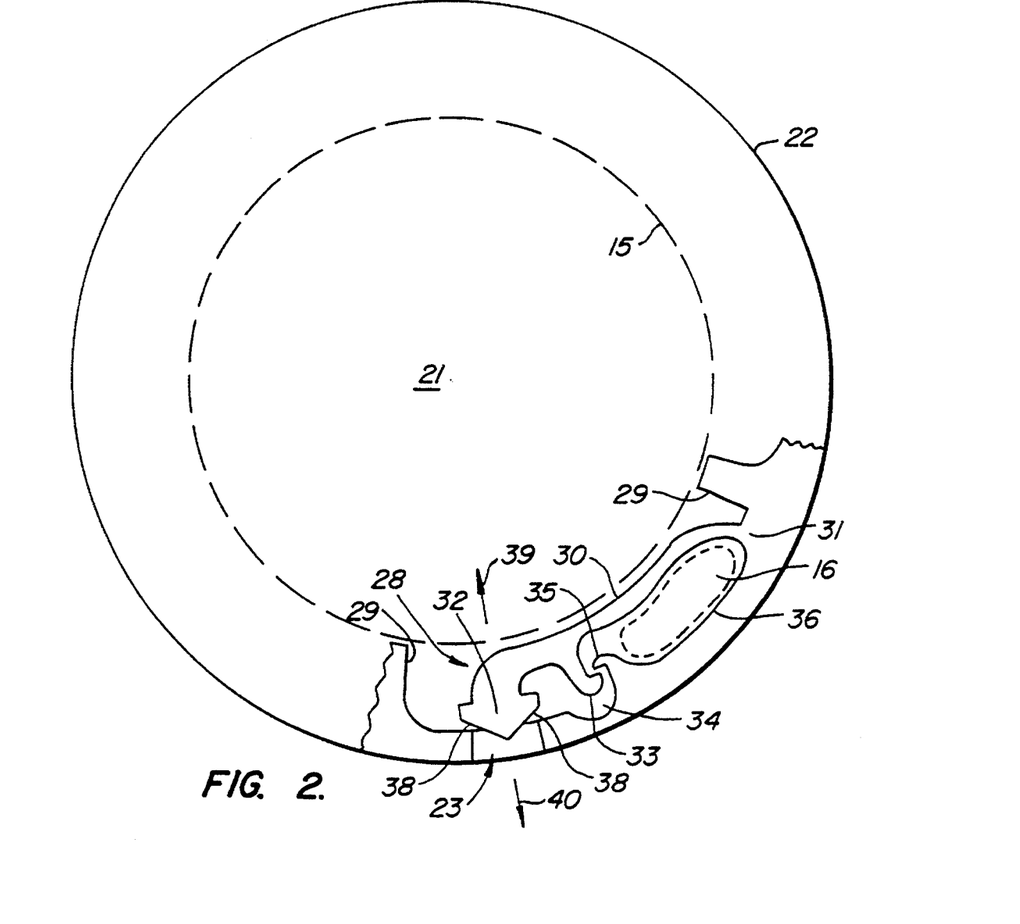
FIG. 2 is a planar view of an angular segment of one portion of the catheter depicted in FIG. 1.

The first example is depicted in FIGS. 1 and 2. FIG. 1 shows the distal end of the catheter in this example is shown in disassembled and exploded form. The catheter body is formed in three parts—an elongate shaft 11 which comprises the bulk of the catheter, a ring 12 which abuts the elongate shaft at the distal end of the shaft, and a sleeve 13 which encircles both the end of the shaft 11 and the ring 12, securing the ring to the shaft. Construction of the catheter in three parts promotes ease of manufacture, and permits a high degree of precision in the formation of the lumens, ports and closures, as discussed below, on a miniature scale.

The distal end 14 of the shaft 11 shows the arrangement of the lumens, each of which extends the full length of the shaft. The primary lumen 15 is coaxial with the shaft, i.e., it shares a common central axis with the shaft. The primary lumen 15 has the largest cross-sectional area of all lumens in the shaft. The secondary lumens 16 in this example are four in number, distributed around the periphery of the primary lumen and equally spaced. Each of these secondary lumens is of considerably smaller cross-sectional area than the primary lumen.

The cross-sectional geometries of the lumens are not critical and may vary. The primary lumen preferably has a circular cross section for purposes of maximizing the ratio of cross section to perimeter length and thereby minimizing the shear force on fluid passing through the lumen. This will minimize the pressure loss of the fluid along the length of the catheter, since the fluid will typically be a liquid such as saline. The secondary lumens will function effectively with a flattened or oblong cross section, which will permit them to transmit pressure adequately while still leaving a large segment of the catheter cross section for the primary lumen. Since the pressure transmission fluid in the secondary lumens remains substantially static regardless of the pressure, there is less of a concern in regard to fluid friction and pressure loss than in the primary lumen.

The number of secondary lumens and their arrangement around the primary lumen, and consequently the number and arrangement of jets at the distal end of the catheter, as described below, may vary. The catheter will function in accordance with the invention with as few as one secondary lumen and associated jet. Such a jet would produce a reaction force in one direction only. Changes of direction are then accomplished by rotating the catheter from its proximal end. In most applications, however, best results will be obtained with a total of 3 to 12 secondary lumens and associated jets, spaced at substantially regular intervals. In preferred constructions, the lumens and jets will number from 4 to 8. The lumens may be spaced apart from each other at regular intervals, or combined in pairs which are spaced apart at regular intervals, or other similar arrangements. The arrangement, in any event, will be one which permits a selection of any single jet or pair of adjacent jets to produce a reaction force in any desired direction without rotation of the catheter.

The ring 12 contains the lateral apertures which form the jets, as well as the closures which open and close the jets. These elements and their operation are best seen in the enlarged section of the ring as shown in FIG. 2. The central opening 21 of the ring is aligned with and open to the primary lumen 15 of the catheter shaft. The outer wall 22 of the ring contains the apertures 23 which form the jets, ejecting fluid radially outward. The sleeve 13 which fits over the ring and the catheter shaft (FIG. 1) contains further apertures 25 which are aligned with the apertures 23 in the ring when the parts are assembled. In the embodiment shown in these drawings, the ring apertures 23 are four in number, as are the sleeve apertures 25, one corresponding to each of the secondary lumens. Also in this embodiment, the ring apertures 23 are rectangular slits which open on one face of the ring (in this case the distal face 27).

One closure 28 is associated with each ring aperture, and as shown in FIG. 2, the closures are separated by partitions 29. Each closure is formed as a lever 30 with a fulcrum 31 at one end and a stopper 32 at the other. Pivoting of the lever occurs about a pivot axis which passes through the fulcrum 31 in the direction perpendicular to the plane of the Figure and thereby parallel to the longitudinal axis of the catheter. The stopper 32 is aligned with the ring aperture 23 and is shaped to seal off the aperture when lowered into it. Attached to the lever at a location between its two ends is a hook 33 which is received in a recess 34 within which the hook travels back and forth in approximately the radial direction of the ring as the lever pivots. In its raised position (the position shown in the drawing), the hook 33 engages a complementary hook 35 which extends inward from the outer wall 22 of the ring and serves as a stop for the range of motion of the mobile hook 33. The complementary contacting surfaces of these hooks also serve as a seal against the passage of fluid when the hooks are engaged.

The portion of the lever extending from the fulcrum 31 to the hook 33 together with the facing portion of the outer wall 22 of the ring form an enclosure 36. When the parts are assembled, the enclosure 36 is enclosed at its proximal end by the distal end 14 of the catheter shaft 11 (see FIG. 1), and at its distal end by a shoulder 37 at the distal end of the sleeve. Each of these enclosures 36 is in axial alignment with one of the secondary lumens 16, whose opening is shown in dashed outline in FIG. 2. When the pressure in the secondary lumen 16 exceeds the pressure in the primary lumen 21 to cause a pressure differential across the lever 30, the enclosure expands until the hooks 33, 35 engage, and the lever is pushed outward toward the center of the ring. This movement of the lever in turn unseats the stopper 32 from the aperture 23. When the pressure in the secondary lumen is released, the lever returns to its original position, reseating the stopper against the aperture. The direction of motion of the lever and hence the stopper is indicated by the arrows 39, 40.

Return of the stopper to the seated position against the aperture may be achieved by a reverse pressure differential created by lowering the pressure in the secondary lumen below that in the primary lumen. Alternatively, the material of construction of the lever 30 and/or its shape and that of the fulcrum may be selected or designed to cause the lever to return to the closed position upon the relaxation of forces in contact with it. The stopper would thus automatically reseat upon relaxation of the pressure in the secondary lumen. The ability to reseat independently may be enhanced if the contacting hooks 33, 35 permit a slow leakage of the pressurization fluid past them, thereby releasing the pressure in the enclosure 36 when the supply pressure is removed.

When the stopper 31 is seated against the aperture in this example, the seating is enhanced by angled lateral surfaces 38 on the stopper. These angled surfaces amplify changes in the width of the opening relative to the lowering or raising of the stopper.

The closures 28 shown in FIGS. 1 and 2 thus act in response to pressure signals transmitted through the secondary lumens 16, the pressure signals being periods of high or low pressures relative to the pressure of the jet fluid in the primary lumen 15, the periods being of controlled duration. A high pressure in one secondary lumen will unseat the stopper 32 and turn on the associated jet, whereas a low pressure will close the stopper and turn off the jet. The independent transmission of these pressure signals permits independent operation of the closures, and jets are emitted selectively as desired to achieve the directional steering of the catheter tip by reaction force.

In the embodiment shown in FIG. 2, the lever 30 and the connecting fulcrum 31 where the lever is joined to the outer wall 22 of the ring is preferably constructed and shaped such that the stopper 32 is seated in the aperture 23 in the absence of a pressure differential. This is a "normally-closed" closure. For normally-closed closures in general, positive pressure signals are needed to activated the respective jets. As an alternative to the structure shown in FIGS. 1 and 2, the fulcrum of the closure (and hence its point of attachment to the ring 22) may be situated in the center of the lever, with the enclosure 36 on one side and the stopper 32 on the other. A positive pressure in the secondary lumen 16 will then close the stopper rather than open it, and the closure will be "normally-open" rather than "normally-closed."

Further alternatives are those in which the lever 30 is positioned further toward the outer wall 22 of the ring, placing the enclosure 36 between the secondary lumen 16 and the outer wall 22. This will require an additional partition along the inside rim of the ring to complete the enclosure. Here as well, the fulcrum will either be at the center of the lever or at one end. Alternatives to the use of a lever, although still operating in response to pressure signals transmitted along the length of the catheter, may also be devised. The stopper may for example be an inflatable bladder positioned to close the aperture only when inflated. Still further constructions and arrangements utilizing the underlying concepts of this invention will be apparent to those skilled in the art.

The ring 12 with its lateral apertures and closures can be manufactured in a variety of ways. Micromachining methods such as those used in the fabrication of semiconductor chips are particularly useful. Examples are:

(1) Laser micromachining of a blank disk to form the various openings and contours by etching or ablation;
(2) Thick film deposition, i.e., the deposition of multiple layers of particles on a substrate through a mask, using the process of physical vapor deposition, followed by removal of the layers from the substrate and the mask;

(3) Chemical vapor deposition over a substrate, again through a mask;

(4) Ion vapor deposition, again through a mask; and (5) Metal plating, using selective buildup methods. A variety of substrates may be used for the deposition and plating procedures. A preferred substrate is silicon.

Figure 3:
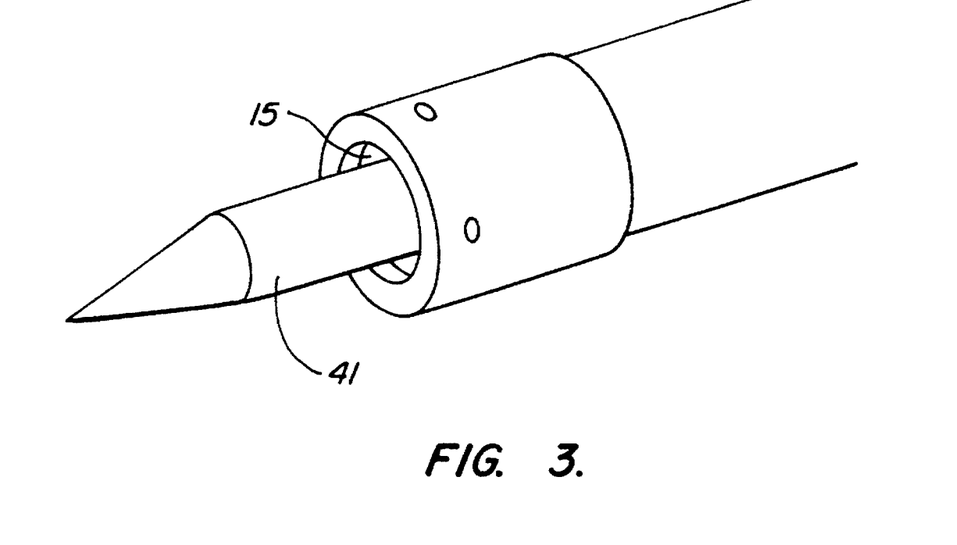
FIG. 3 is a perspective view of the distal end of a second example of a catheter constructed in accordance with the present invention.
Figure 4:
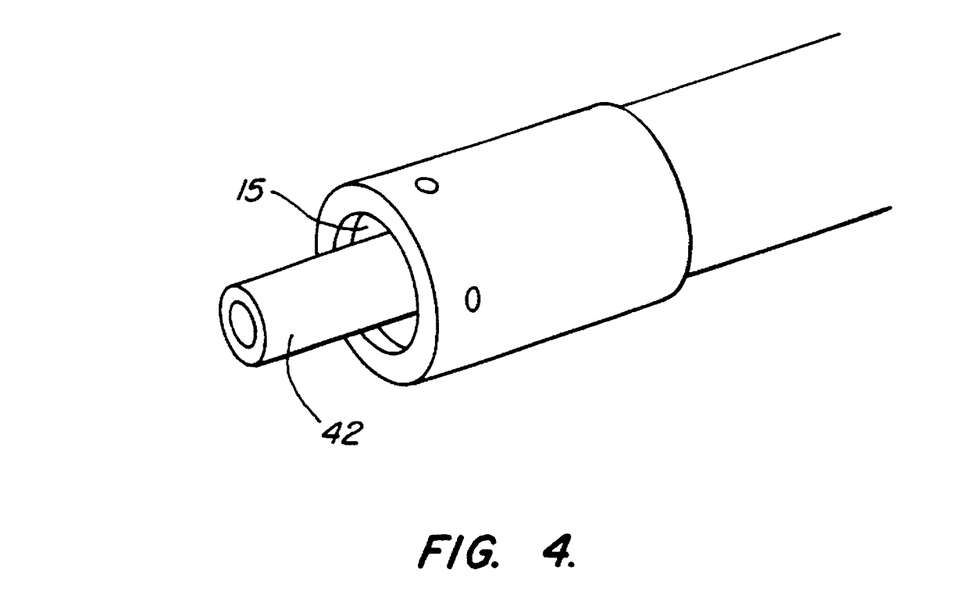
FIG. 4 is a perspective view of the distal end of a third example of a catheter constructed in accordance with the present invention.

In certain embodiments of the invention, the catheter contains functional elements either for the transmission of diagnostics and sensor signals from the distal end to the proximal end of the catheter, or for performing a therapeutic function at the distal end, or both. The functional element may be mounted on an axial shaft 41 as shown in FIG. 3, passing through the primary lumen 15, or it may itself be a separate lumen 42 as shown in FIG. 4, either coaxial with or offset from the primary lumen 15. For signal transmitting purposes, the functional element may be a radiopaque marker, a fluoroscopic contrast agent retained in a reservoir such as a microballoon, an optical fiber, or an ultrasonic transducer. For therapeutic purposes, the functional element may be a cutting blade, an abrading element such as a grinding burr, a laser ablation element, an angioplasty balloon or simply a lumen for delivering a therapeutic fluid which may be either a drug or an abrading solution or slurry. Other possibilities will be readily apparent to those skilled in the art.

Figure 5:
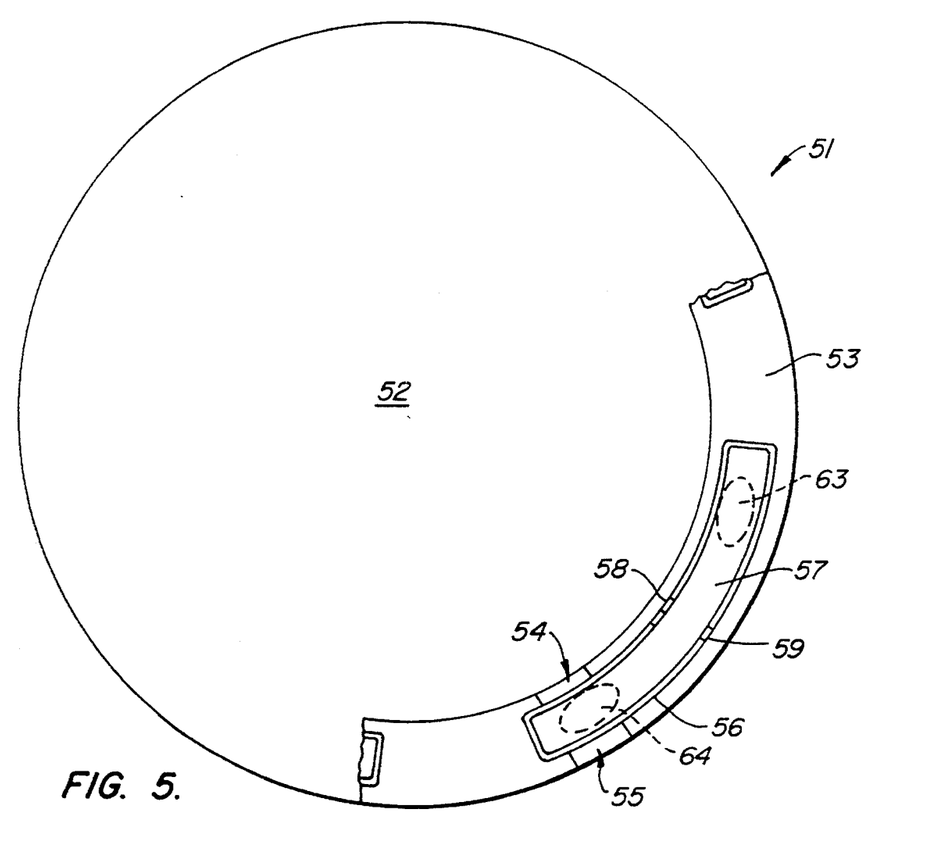
FIG. 5 is a planar view of an angular segment of a fourth example of a catheter within the scope of the invention.
Figure 6:
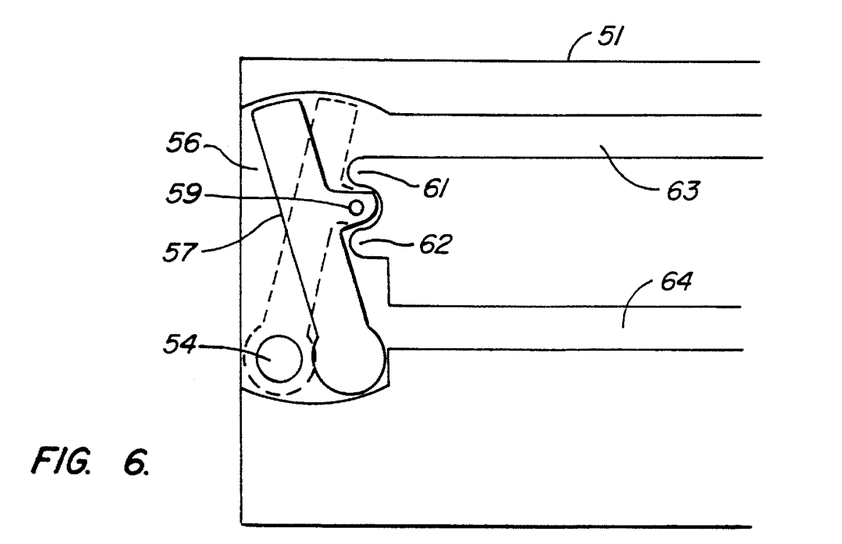
FIG. 6 is a side cutaway view of the catheter of FIG. 6.

FIGS. 5 and 6 represent an embodiment of the invention which is similar in certain ways to the embodiment shown in FIGS. 1 and 2, but differs in the direction of rotation of the strip containing the lever and closure.

The catheter 51 has a central passage or primary lumen 52 enclosed at the distal end by a ring 53. Each jet is formed by a pair of radially aligned apertures 54, 55 on either side of a chamber 56 formed within the wall of the ring 53. Inside the chamber is a lever arm 57 adjoined to the internal walls of the chamber by pivot posts 58, 59, which permit rotation of the lever arm about an axis directed radially relative to the catheter.

As shown in FIG. 6, the lever arm pivots between two positions, one shown in solid lines in which one end 60 of the lever arm (the stopper end) lies between the two apertures 54, 55 and thereby shuts off the jet emerging through those apertures, and the other shown in dashed lines in which the stopper end 60 is clear of the two apertures, causing the jet to flow outward from the primary lumen 52. The range of movement of the lever arm 57 is restricted by blocking posts 61, 62. The position of the lever arm is governed by pressurized fluid fed to the chamber 56 at either side of the pivot axis by lumens 63, 64. By using separate supplies of pressurized fluid for each side of the lever arm, this construction does not rely on the pressure in the primary lumen 52 to maintain the arm in any one position. The individual supplies may be regulated such that the apertures are either normally-open or normally-closed.

Figure 7:
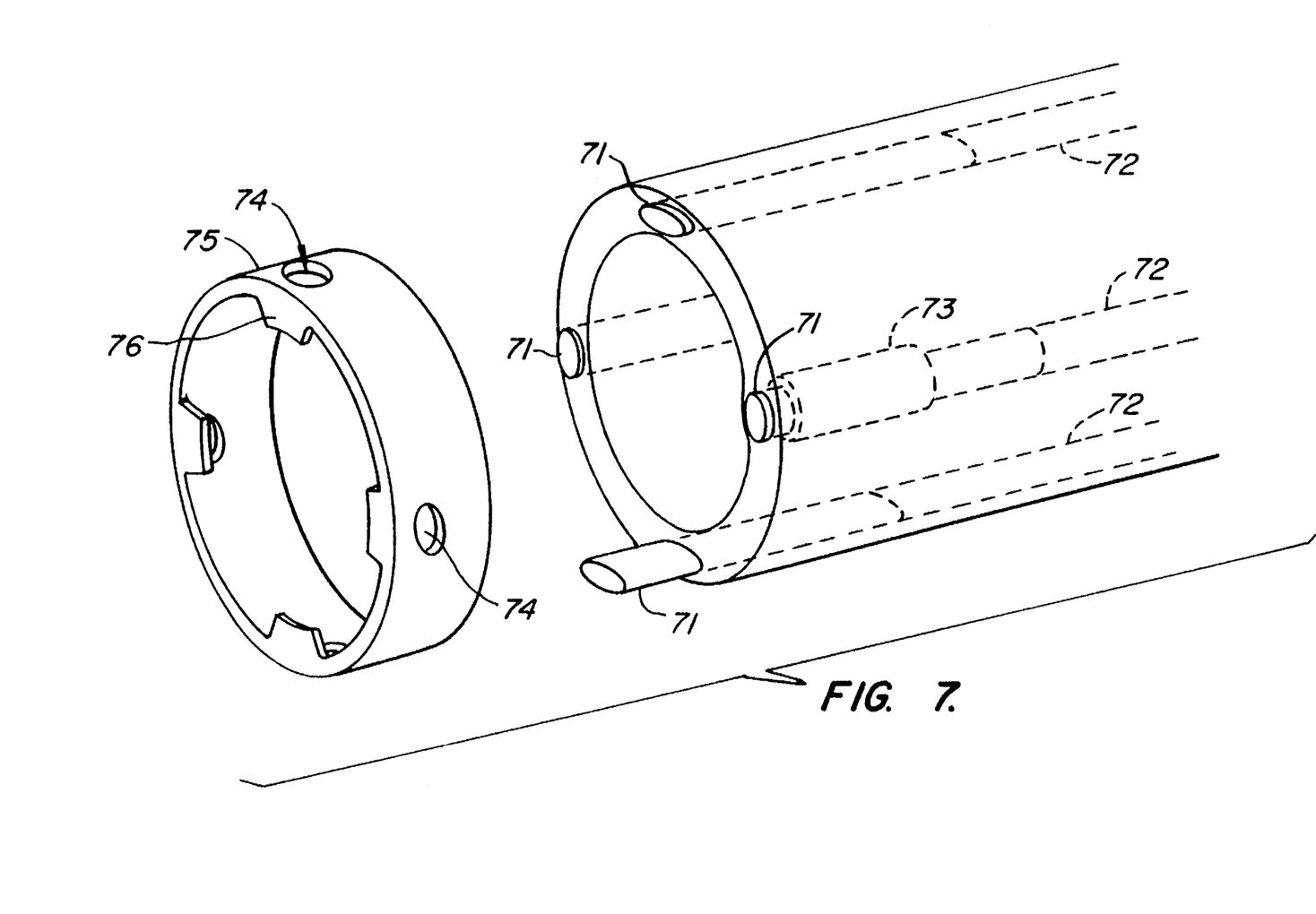
FIG. 7 is an exploded view in perspective of a fifth example within the scope of the invention.

FIG. 7 illustrates an embodiment which does not utilize levers, but instead utilizes axially movable rods or pistons 71. The pistons reside in lumens 72 in which they are sufficiently loose to permit them to move back and forth axially. They may be forced forward by fluid pressure in the lumens or by electromagnetic means such as by the use of coils 73 serving as miniature solenoid valves. Alternatively, the coils may be used to retract the pistons until fluid pressure forces them forward. In FIG. 7, the lowermost piston is shown in an extended position while the remaining three pistons are in a retracted position.

When in the extended position, the pistons 71 cover apertures 74 in the distal ring 75 of the catheter. Stops 76 at the distal terminus of the ring limit the range of motion of the pistons and retain them in the catheter. Pistons which are retracted are clear of the apertures, thereby permitting jets to emerge through those apertures.

Figure 8:
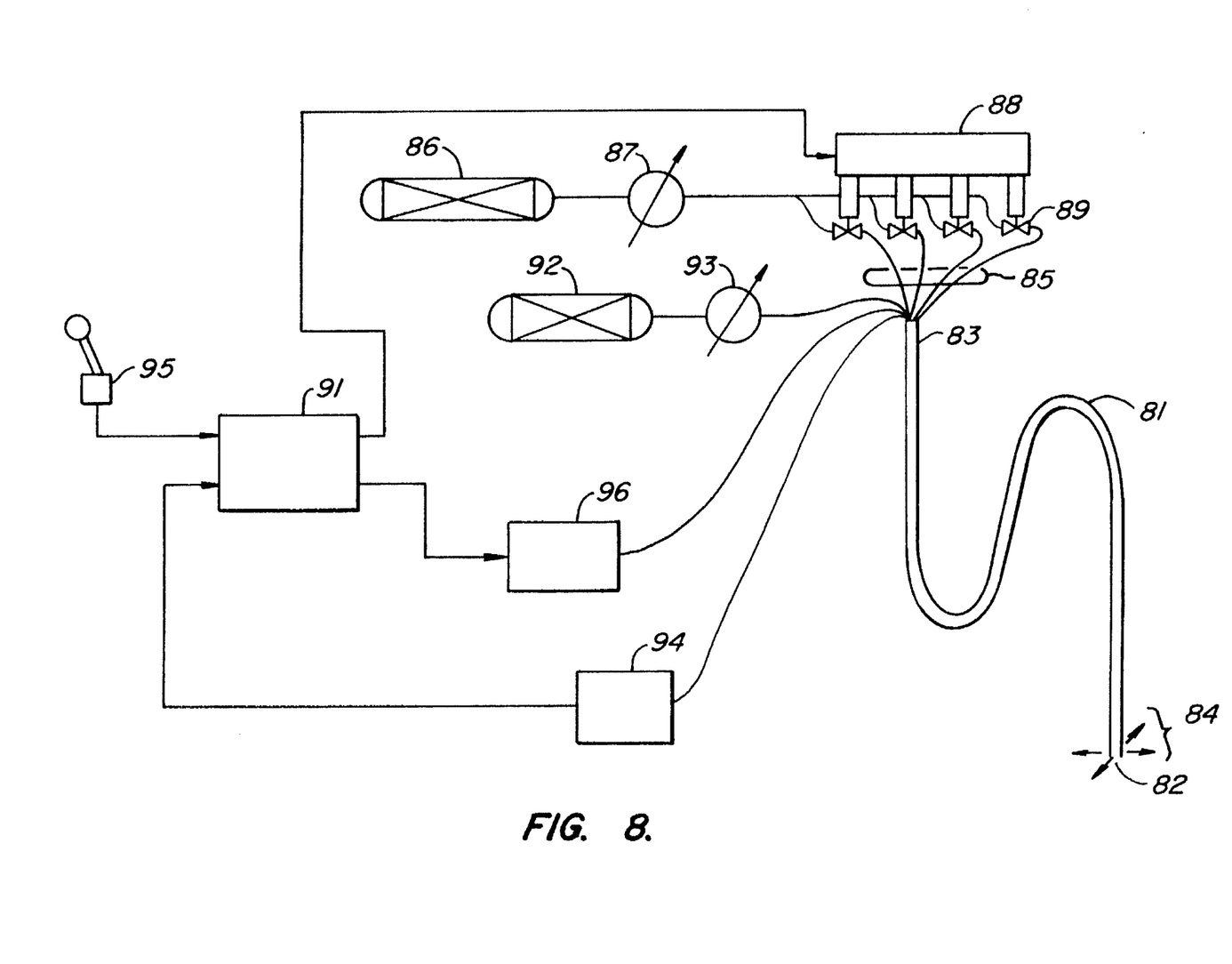
FIG. 8 is a combination block diagram and schematic drawing of a system incorporating a catheter in accordance with the present invention.

A system for operating a steerable catheter in accordance with this invention and for supplying all necessary fluids is shown in FIG. 8. The catheter 81 has distal 82 and proximal 83 ends, and contains four secondary lumens, thereby supplying four jets 84. Although four secondary lumens are included in this drawing, this number is used for illustrative purposes only. The actual number may be other than four, depending on the type of closure and its operation, as well as the number of jets, as explained above.

Four supply conduits 85 are connected to the proximal end of the catheter, one such conduit feeding each of the four secondary lumens. Pressurized gas or liquid for use in these conduits originates from a common source 86, which may be a reservoir with a downstream pump, a pressurized container, or any other means of supply appropriate for the desired pressure. The pressurized gas or liquid passes through a safety regulator 87 which protects the system from overpressurized fluid. From the regulator, the fluid passes through a manifold 88, then to a series of four valves 89 arranged in series, one of these valves per supply conduit 85.

The valves are individually controlled by control signals from a computer 91 of conventional programming for catheter operation. The valves 89 are normally open in this particular embodiment, and close upon receiving pulse-modulated signals from the computer. Referring to the embodiment of FIGS. 1 and 2 as an example, closure of any single valve results in opening of the corresponding jet closure 28 at the distal end of the catheter, and ejection of fluid from the jet.

The fluid for the jets themselves is supplied by a separate fluid source 92, which again may be a reservoir with a downstream pump, a pressurized container, or any other means of supply appropriate for the desired pressure. For this source as well, a safety regulator 93 protects the system from overpressurization.

The four valves 89 may be solenoid valves, pressure-operated valves or any other type of valve controllable by control signals from a computer. The valves preferably have a high frequency response to cause them to open and close rapidly in response to the control signals.

In one application of the system shown in FIG. 8, the computer 91 emits control signals to the valves 89 based on information from a sensor affixed to the catheter 81 near its distal end. The sensor may be an ultrasonic transducer, an optical fiber, or any other of the variety of known means for collecting information at the distal end of the catheter and transmitting it to the proximal end. The information from the sensor is transmitted backward through the catheter through an imaging system 94 and from there to the computer 91. When the catheter is positioned in a blood vessel, for example, signals from the sensor are processed by the imaging system 94 to generate a virtual map, or two-dimensional or three-dimensional image of the interior of the vessel and the position of the catheter inside the vessel. The information produced by the imaging system may for example be a tabulation of distances from the catheter to the vessel wall as a function of radial angle. Alternatively, the information may be a video image of the vessel surrounding the catheter.

The information generated by the imaging system 94 can be used by the operator to direct the catheter tip along a desired path through manual operator input. To accomplish this, the operator uses a manual control device 95 such as a joystick, a mouse, a touch-sensitive display panel, or any other known type of directional control device. Signals from the control device 95 will be transmitted to the computer which will then calculate the appropriate sequence of control pulses and transmit them to the valves 89 according to the calculated sequence.

This is but one of a variety of ways in which a computer system such as that shown in FIG. 8 can be used. The system may also be used to direct the catheter along a predetermined path, with the computer programmed accordingly prior to the insertion of the catheter. A further use would be to integrate the system with therapeutic action such as cutting, abrasion or ablation. For this use, the therapeutic element will be incorporated into the catheter construction as described above and functioning of the element will be controlled by an external control unit 96. The physician will designate undesirable tissue or the presence of an undesired deposit on an image generated by the imaging system. The computer is then programmed to generate a series of cutting or ablation paths until the specified tissue or deposit is destroyed or removed.

The foregoing is offered primarily for purposes of illustration. It will be readily apparent to those skilled in the art that the components of the system, their configuration, arrangement and operation can be further modified or substituted in various ways without departing from the spirit and scope of the invention.

What is claimed is:

1. A steerable catheter, comprising:

an elongate catheter body having proximal and distal ends, a longitudinal axis and a cylindrical side wall;

a lumen extending the length of said catheter body;

at least one radial port at the distal end of said catheter body in said catheter body in said cylindrical side wall, said radial port communicating said lumen with the exterior of said catheter body;

at least one closure mounted to said catheter body at said distal end, said closure positioned to engage said radial port, said closure constructed to be driven by a signal selected from the group consisting of a fluid pressure signal and an electrical signal, said signal transmitted along the length of said catheter body from said proximal end; and signal transmission means for transmitting signals capable of driving said closure to said closure from said proximal end of said catheter body to effect opening and closing of said radial port.

2. A steerable catheter in accordance with claim 1 in which said lumen is defined as a primary lumen, said closure is constructed to be driven by a fluid pressure signal, and said signal transmission means comprises a secondary lumen communicating fluid pressure from said proximal end of said catheter body to said closure.

3. A steerable catheter in accordance with claim 1 in which said closure is constructed to be driven by an electrical signal, and said signal transmission means comprises an electrical conduit extending the length of said catheter body.

4. A steerable catheter in accordance with claim 2 in which said signal transmission means further comprises:

a source of pressurized fluid; and a valve external to said steerable catheter, joining the proximal end of said secondary lumen to said source of pressurized fluid.

5. A steerable catheter in accordance with claim 1 in which said lumen is defined as a primary lumen, said closure comprises a stopper affixed to lever means pivotally mounted to said catheter body, and said signal transmission means comprises a secondary lumen communicating fluid pressure to said lever means.

6. A steerable catheter in accordance with claim 5 further comprising a flexible linkage joining said closure pivotally to said catheter body, said linkage serving as a fulcrum for said lever means.

7. A steerable catheter in accordance with claim 5 in which said lever means is mounted to said catheter body for pivoting about an axis parallel to said longitudinal axis of said catheter body.

8. A steerable catheter in accordance with claim 5 in which said lever means is mounted to said catheter body for pivoting about an axis which is radial relative to said catheter body.

9. A steerable catheter in accordance with claim 1 in which said closure comprises a piston movable parallel to said longitudinal axis, between a first position in which a lateral surface of said piston closes said radial port, and a second position in which said piston clears said radial port, and said signal transmission means comprises means for communicating an electrical signal to govern the position of said piston.

10. A steerable catheter in accordance with claim 1 in which said closure comprises a piston movable parallel to said longitudinal axis, between a first position in which a lateral surface of said piston closes said radial port, and a second position in which said piston clears said radial port, and said signal transmission means comprises fluid pressure transmission means for communicating fluid pressure to drive said piston.

11. A steerable catheter in accordance with claim 1 comprising a plurality of said radial ports distributed around the circumference of said cylindrical side wall, and a plurality of said closures, one such closure positioned to engage each of said radial ports, and said signal transmission means is means for communicating signals independently to each of said closures.

12. A steerable catheter in accordance with claim 11 in which said lumen is defined as a primary lumen, and said signal transmission means comprises a plurality of secondary lumens, at least one such secondary lumen communicating said proximal end of said catheter body to each of said closures.

13. A steerable catheter in accordance with claim 12 in which said primary lumen is coaxial with said catheter body, and said secondary lumens are distributed around the periphery of said primary lumen.

14. A steerable catheter in accordance with claim 12 in which said signal transmission means is pressure communication means further comprising:

a source of pressurized fluid; and a plurality of valves external to said steerable catheter, one of said valves joining the proximal end of each of said secondary lumens to said source of pressurized fluid.

15. A steerable catheter in accordance with claim 12 in which each said closure comprises a stopper affixed to lever means pivotally mounted to said catheter body; and in which at least one such secondary lumen communicates fluid pressure to each said lever means.

16. A steerable catheter in accordance with claim 15 further comprising a plurality of flexible linkages, one such flexible linkage joining each said closure pivotally to said catheter body, and each said linkage separating the stopper from the lever means of said closure.

17. A steerable catheter in accordance with claim 11 in which said lumen is defined as a primary lumen, and said fluid pressure communication means comprises a plurality of secondary lumens, at least one such secondary lumen communicating said proximal end of said catheter body to each of said closures, and in which said lever means form movable boundary segments between said primary lumen and said secondary lumens at said distal end of said catheter body.

18. A steerable catheter in accordance with claim 11 in which said plurality of radial ports comprises from 3 to 12 radial ports distributed around the circumference of said catheter body at said distal end at substantially regular intervals.

19. A steerable catheter in accordance with claim 11 in which said plurality of radial ports comprises from 4 to 8 radial ports distributed around the circumference of said catheter body at said distal end at substantially regular intervals.

20. A steerable catheter in accordance with claim 11 in which said closures are normally closed, such that said closures close said radial ports in the absence of a signal being transmitted through said signal transmission means.

21. A steerable catheter in accordance with claim 11 in which said closures are normally closed, such that said closures maintain said radial ports closed in the absence of a signal being transmitted through said signal transmission means.

22. A steerable catheter in accordance with claim 1 in which said signal is defined as a closure-driving signal, and said steerable catheter further comprises an element transmitting a detectable signal, said element affixed to said distal end to permit monitoring of the location of said distal end.

23. A steerable catheter in accordance with claim 22 in which said element further permits imaging of tissue surrounding the location of said distal end.

24. A steerable catheter in accordance with claim 22 in which said signal transmitting element is a member selected from the group consisting of a radiopaque marker, a fluoroscopic contrast agent, a tip of an optical fiber, an ultrasonic transducer, and an element emitting electrical energy for etching or ablation.

25. A steerable catheter in accordance with claim 1 further comprising a therapeutic element affixed to said distal end.

26. A steerable catheter in accordance with claim 25 in which said therapeutic element is a member selected from the group consisting of a cutting element, an abrading element, a laser ablation element and an angioplasty balloon.

27. A steerable catheter in accordance with claim 1 further comprising a therapeutic fluid supply lumen for supplying a therapeutic fluid to said distal end of said catheter.

* * * * *